United States Patent
Chambers

(10) Patent No.: US 10,383,725 B2
(45) Date of Patent: Aug. 20, 2019

(54) HEART CHAMBER PROSTHETIC VALVE IMPLANT WITH BASE, MESH AND DOME SECTIONS WITH SINGLE CHAMBER ANCHORING FOR PRESERVATION, SUPPLEMENTATION AND/OR REPLACEMENT OF NATIVE VALVE FUNCTION

(71) Applicant: 4C Medical Technologies, Inc., Brooklyn Park, MN (US)

(72) Inventor: Jeffrey W. Chambers, Maple Grove, MN (US)

(73) Assignee: 4C Medical Technologies, Inc., Brooklyn Park, MN (US)

( * ) Notice: Subject to any disclaimer, the term of this patent is extended or adjusted under 35 U.S.C. 154(b) by 0 days.

(21) Appl. No.: 15/673,965

(22) Filed: Aug. 10, 2017

(65) Prior Publication Data

US 2018/0042719 A1 Feb. 15, 2018

Related U.S. Application Data

(60) Provisional application No. 62/373,541, filed on Aug. 11, 2016, provisional application No. 62/373,560, (Continued)

(51) Int. Cl.
*A61F 2/24* (2006.01)
(52) U.S. Cl.
CPC .......... *A61F 2/2409* (2013.01); *A61F 2/2412* (2013.01); *A61F 2/2418* (2013.01);
(Continued)

(58) Field of Classification Search
CPC .............................. A61F 2/2418; A61F 2/2487
See application file for complete search history.

(56) References Cited

U.S. PATENT DOCUMENTS

| 4,503,569 A | 3/1985 | Dotter |
| 4,733,665 A | 3/1988 | Palmaz |

(Continued)

FOREIGN PATENT DOCUMENTS

| CN | 100444811 C | 12/2008 |
| DE | 10201021354 | 11/2011 |

(Continued)

OTHER PUBLICATIONS

International Search Report and the Written Opinion of the International Searching Authority, dated Oct. 18, 2017, for PCT Application No. PCT/US2017/046448, filed Aug. 11, 2017.
(Continued)

*Primary Examiner* — Suba Ganesan
(74) *Attorney, Agent, or Firm* — Barnes & Thornburg LLP; Jeffrey R. Stone

(57) ABSTRACT

Various embodiments of the present invention comprise a single-chamber collapsible and expandable prosthetic valve implant device comprising the following capabilities: (1) preservation of native valve functionality; (2) initial preservation of native valve functionality with subsequent full replacement of native valve functionality; (3) full replacement of native valve functionality; and/or (4) mitigation of the prolapsing distance of the dysfunctional leaflets by preventing the anterior excursion of the prolapsing leaflets above the upper annular surface and into the left atrial chamber in order to preserve native leaflet functionality for as long as possible. The expanded and implanted device does not extend beyond the boundaries of the subject heart chamber, e.g., the left atrium, thereby enabling the preservation of any remaining native valve functionality with subsequent full replacement of native valve functionality if and when needed.

20 Claims, 9 Drawing Sheets

Related U.S. Application Data filed on Aug. 11, 2016, provisional application No. 62/373,551, filed on Aug. 11, 2016.

(52) U.S. Cl.
CPC .......... *A61F 2/2442* (2013.01); *A61F 2/2454* (2013.01); *A61F 2/2463* (2013.01); *A61F 2/2469* (2013.01); *A61F 2/2487* (2013.01); *A61F 2210/0014* (2013.01); *A61F 2230/0069* (2013.01); *A61F 2250/0048* (2013.01)

(56) References Cited

U.S. PATENT DOCUMENTS

| | | |
|---|---|---|
| 5,693,083 A | 12/1997 | Baker et al. |
| 5,957,949 A | 9/1999 | Leonhardt et al. |
| 5,968,070 A | 10/1999 | Bley et al. |
| 6,123,723 A | 9/2000 | Konya et al. |
| 6,319,281 B1 | 11/2001 | Patel |
| 6,371,983 B1 | 4/2002 | Lane |
| 6,458,153 B1 | 10/2002 | Bailey |
| 6,494,909 B2 | 12/2002 | Greenhalgh |
| 6,503,272 B2 | 1/2003 | Duerig et al. |
| 6,540,782 B1 | 4/2003 | Snyders |
| 6,589,275 B1 | 7/2003 | Ivancev et al. |
| 6,702,826 B2 | 1/2004 | Liddicoat et al. |
| 6,730,118 B2 | 5/2004 | Spenser et al. |
| 6,790,231 B2 | 9/2004 | Liddicoat et al. |
| 6,790,237 B2 | 9/2004 | Stinson |
| 6,821,297 B2 | 11/2004 | Snyders |
| 6,840,957 B2 | 1/2005 | DiMatteo et al. |
| 7,011,671 B2 | 3/2006 | Welch |
| 7,044,966 B2 | 5/2006 | Svanidze et al. |
| 7,153,324 B2 | 12/2006 | Case et al. |
| 7,276,077 B2 | 10/2007 | Zadno-Azizi et al. |
| 7,291,168 B2 | 11/2007 | Macoviak et al. |
| 7,510,572 B2 | 3/2009 | Gabbay |
| 7,510,575 B2 | 3/2009 | Spenser et al. |
| 7,611,534 B2 | 11/2009 | Kapadia et al. |
| 7,959,666 B2 | 6/2011 | Salahieh et al. |
| 7,959,672 B2 | 6/2011 | Salahieh et al. |
| 8,012,201 B2 | 9/2011 | Lashinski et al. |
| 8,057,493 B2 | 11/2011 | Goldfarb et al. |
| 8,109,996 B2 | 2/2012 | Stacchino et al. |
| 8,142,492 B2 | 3/2012 | Forster et al. |
| 8,252,051 B2 | 8/2012 | Chau et al. |
| 8,308,798 B2 | 11/2012 | Pintor et al. |
| 8,348,995 B2 | 1/2013 | Tuval et al. |
| 8,449,599 B2 | 5/2013 | Chau et al. |
| 8,535,373 B2 | 9/2013 | Stacchino et al. |
| 8,603,159 B2 | 12/2013 | Seguin et al. |
| 8,636,764 B2 | 1/2014 | Miles et al. |
| 8,764,793 B2 | 7/2014 | Lee |
| 8,795,357 B2 | 8/2014 | Yohanan et al. |
| 8,808,356 B2 | 8/2014 | Braido et al. |
| 8,828,043 B2 | 9/2014 | Chambers |
| 8,828,051 B2 | 9/2014 | Javois et al. |
| 8,845,711 B2 | 9/2014 | Miles et al. |
| 8,845,722 B2 | 9/2014 | Gabbay |
| 8,858,620 B2 | 10/2014 | Salahieh et al. |
| 8,956,402 B2 | 2/2015 | Cohn |
| 9,060,857 B2 | 6/2015 | Nguyen et al. |
| 9,072,603 B2 | 7/2015 | Tuval et al. |
| 9,168,133 B2 | 10/2015 | Spenser et al. |
| 9,173,737 B2 | 11/2015 | Hill et al. |
| 9,220,594 B2 | 12/2015 | Braido et al. |
| 9,226,820 B2 | 1/2016 | Braido et al. |
| 9,289,292 B2 | 3/2016 | Anderl et al. |
| 9,301,836 B2 | 4/2016 | Buchbinder et al. |
| 9,320,599 B2 | 4/2016 | Salahieh et al. |
| 9,351,831 B2 | 5/2016 | Braido et al. |
| 9,351,832 B2 | 5/2016 | Braido et al. |
| 9,358,108 B2 | 6/2016 | Bortlein et al. |
| 2005/0096739 A1 | 5/2005 | Cali et al. |
| 2005/0113861 A1 | 5/2005 | Corcoran et al. |
| 2005/0197694 A1 | 9/2005 | Pai et al. |
| 2006/0020327 A1 | 1/2006 | Lashinski et al. |
| 2006/0287719 A1 | 12/2006 | Rowe et al. |
| 2009/0099647 A1 | 4/2009 | Glimsdale et al. |
| 2010/0217382 A1* | 8/2010 | Chau .............. A61F 2/2418 623/1.26 |
| 2011/0054515 A1 | 3/2011 | Bridgeman et al. |
| 2013/0138138 A1 | 5/2013 | Clark et al. |
| 2013/0304197 A1 | 11/2013 | Buchbinder et al. |
| 2014/0005778 A1 | 1/2014 | Buchbinder et al. |
| 2014/0018841 A1 | 1/2014 | Peiffer et al. |
| 2014/0031928 A1 | 1/2014 | Murphy et al. |
| 2014/0074151 A1 | 3/2014 | Tischler et al. |
| 2014/0114340 A1 | 4/2014 | Zhou et al. |
| 2014/0135817 A1 | 5/2014 | Tischler et al. |
| 2014/0142612 A1 | 5/2014 | Li et al. |
| 2014/0188157 A1 | 7/2014 | Clark |
| 2014/0257467 A1 | 9/2014 | Lane et al. |
| 2014/0277074 A1 | 9/2014 | Kaplan et al. |
| 2014/0296909 A1 | 10/2014 | Heipl et al. |
| 2015/0039083 A1 | 2/2015 | Rafiee |
| 2015/0127097 A1 | 5/2015 | Neumann et al. |
| 2015/0173897 A1 | 6/2015 | Raanani et al. |
| 2015/0196300 A1 | 7/2015 | Tischler et al. |
| 2015/0223934 A1 | 8/2015 | Vidlund et al. |
| 2015/0257879 A1 | 9/2015 | Bortlein et al. |
| 2015/0257880 A1 | 9/2015 | Bortlein et al. |
| 2015/0257882 A1 | 9/2015 | Bortlein et al. |
| 2016/0051358 A1 | 2/2016 | Sutton et al. |
| 2016/0051362 A1 | 2/2016 | Cooper et al. |
| 2016/0066922 A1 | 3/2016 | Bridgeman et al. |
| 2016/0089238 A1* | 3/2016 | Centola ............... A61F 2/2445 623/2.37 |
| 2016/0100844 A1 | 4/2016 | Li et al. |
| 2016/0158001 A1 | 6/2016 | Wallace et al. |
| 2016/0158007 A1 | 6/2016 | Centola et al. |
| 2016/0242905 A1* | 8/2016 | Chambers ............ A61F 2/2412 |

FOREIGN PATENT DOCUMENTS

| | | |
|---|---|---|
| EP | 2856946 A1 | 8/2005 |
| EP | 2596754 A1 | 5/2013 |
| WO | WO2010/099032 | 9/2010 |
| WO | WO2013/178335 | 12/2013 |
| WO | WO2015/189307 | 12/2015 |
| WO | WO2016/033170 | 3/2016 |

OTHER PUBLICATIONS

International Preliminary Report on Patentability issued in related PCT application No. PCT/US2017/046448, dated Feb. 21, 2019.

\* cited by examiner

WHERE:
α = 90°; AND
D3 = D4

HEART CHAMBER PROSTHETIC VALVE IMPLANT WITH BASE, MESH AND DOME SECTIONS WITH SINGLE CHAMBER ANCHORING FOR PRESERVATION, SUPPLEMENTATION AND/OR REPLACEMENT OF NATIVE VALVE FUNCTION

CROSS-REFERENCE TO RELATED APPLICATIONS

This application claims the benefit of U.S. Provisional Application Ser. No. 62/373,541, filed Aug. 11, 2016 and entitled HEART CHAMBER PROSTHETIC VALVE IMPLANT WITH STENT, SPRING AND DOME SECTIONS, of U.S. Provisional Application Ser. No. 62/373,560 filed Aug. 11, 2016 and entitled HEART CHAMBER PROSTHETIC VALVE IMPLANT WITH STENT, MESH AND DOME SECTIONS, and of U.S. Provisional Application Ser. No. 62/373,551, filed Aug. 11, 2016 and entitled HEART CHAMBER PROSTHETIC VALVE IMPLANT WITH ELEVATED VALVE SECTION, the entirety of each of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to devices and methods for implanting devices within a heart chamber. More specifically, the invention relates to single-chamber anchoring frames comprising an anchoring structure located completely within the single-chamber and a prosthetic valve located for preservation and/or replacement of native valve functionality.

Description of the Related Art

The human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve. See generally FIG. 1.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of. For example, the mitral valve when working properly provides a one-way valving between the left atrium and the left ventricle, opening to allow antegrade flow from the left atrium to the left ventricle and closing to prevent retrograde flow from the left ventricle into the left atrium. This retrograde flow, when present, is known as mitral regurgitation or mitral valve regurgitation.

FIG. 2 illustrates the relationship between the left atrium, annulus, chordae tendineae and the left ventricle relative to the mitral valve leaflets. As is shown, the upper surface of the annulus forms at least a portion of the floor or lower surface of the left atrial chamber, so that for purposes of description herein, the upper surface of the annulus is defined as marking the lower boundary of the left atrial chamber and is represented generally by at least one point A indicating the general position of an implanted object resting or mounted on a designated upper annular surface, the designation of which is discussed in detail infra. In practice, more than one point A may be used to designate the upper annular surface for purposes of locating the anchoring structure and prosthetic valve within the single heart chamber and without interference with the native valve leaflets.

The region of the annulus through which blood flows in a generally downward antegrade direction between the left atrium and left ventricle occurs, but above the point of flexing of the native leaflets is referred to herein as the inner annulus. Reference is made to FIGS. 7A and 7B for a cross-sectional side view of the annulus, native leaflets, the designated upper annular surface and the inner annulus. Note that the designated upper annular surface described above defines the lower boundary of at least a portion of the left atrium. Therefore, the designated upper annular surface may also extend across the annulus itself, e.g., covering the annular plane as known to the skilled artisan. However, the designated upper annular surface may also, as described further below, extend downward (antegrade) into the annulus a distance, but may not extend downwardly (antegrade) beyond the point at which any structure placed at the designated upper annular surface may adversely affect the functionality of the native valve leaflets within the inner annulus, e.g., at the point of flexion of the native valve leaflets.

Native heart valves may be, or become, dysfunctional for a variety of reasons and/or conditions including but not limited to disease, trauma, congenital malformations, and aging. These types of conditions may cause the valve structure to fail to close properly resulting in regurgitant retrograde flow of blood from the left ventricle to the left atrium in the case of a mitral valve failure. FIGS. 3 and 4 illustrate the regurgitant blood flow with a dysfunctional mitral valve. FIG. 4 illustrates a prolapsing native valve with loss of coaptation between the leaflets and the resulting regurgitant blood flow from the left ventricle to the left atrium.

Mitral valve regurgitation is a specific problem resulting from a dysfunctional mitral valve that allows at least some retrograde blood flow back into the left atrium from the right atrium. In some cases, the dysfunction results from mitral valve leaflet(s) that prolapse up into the left atrial chamber, i.e., above the upper surface of the annulus as designated by line or plane A, instead of connecting or coapting to block retrograde flow. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally-adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and transseptal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

In addition, all known prosthetic heart valves are intended for full replacement of the native heart valve. Therefore, these replacement heart valves, and/or anchoring or tethering structures, physically extend out of the left atrial chamber, in the case of mitral valves, and engage the inner annulus and/or valve leaflets, in many cases pinning the native leaflets against the walls of the inner annulus, thereby permanently eliminating all remaining functionality of the native valve and making the patient completely reliant on the replacement valve. In other cases, the anchoring structures extend into the left ventricle and may anchor into the left ventricle wall tissue and/or the sub-annular surface at the top of the left ventricle. Others may comprise a presence in, or engagement with, a pulmonary artery.

Each of the prosthetic valve implant solutions requiring extension, purchase, anchoring, operative and/or fluid communication, operative connection and/or engagement with tissues, valves and/or channels and/or chambers outside of the left atrium with concomitant reduction or elimination of the relevant native valve functionality require improvement. For convenience, we refer to these solutions collectively herein as two-chamber solutions. Generally speaking, when the native valve leaflets retain some functionality, preferred solutions are those that maintain and/or retain the native function of a heart valve, thus supplementation or augmentation of the native valve and its functionality is preferred rather than full replacement.

Obviously, there will be cases when native valve has lost virtually complete functionality before the interventional implantation procedure. In this case the preferred solution will comprise an implant that does not extent outside of, e.g., the left atrium, and that functions to completely replace the native valve function. However, in many other cases, the native valve remains functional to an extent and may, or may not, continue to lose functionality after the implantation procedure. A preferred solution in this case comprises delivery and implantation of a valve device that will function both as a supplemental or augmentation valve without damaging the native leaflets in order to retain native valve leaflet functionality as long as present, while also being fully capable of replacing the native function of a valve that slowly loses most or all of its functionality post-implantation of the prosthetic valve.

Additional problems exist with two-chamber solutions. They are unnecessary bulky and long, making delivery and positioning/recapture/repositioning more difficult from a strictly structural perspective. Further, the two-chamber solutions present difficulties in terms of making the ventricular anchoring and/or tethering connections required to hold position. Moreover, these solutions interfere with the native valve functionality as described above because the device portions that are disposed within the left ventricle must be routed through the annulus, transiting through at least a portion of the inner annulus and native mitral valve, thereby necessarily permanently disrupting, and in some cases eliminating, any remaining coaptation capability and functionality of the native leaflets. In addition, many of the two-chamber solutions generally require an invasive anchoring of some of the native tissue, resulting in unnecessary trauma and potential complication.

Certain inventive embodiments described herein are readily applicable to single or two-chamber solutions, unless otherwise indicated. Moreover, certain embodiments discussed herein may be applied to preservation and/or replacement of native valve functionality generally and are not, therefore, limited to the mitral valve.

Various embodiments of the several inventions disclosed herein address these, inter alia, issues.

DETAILED DESCRIPTION OF THE INVENTION

Figure 1:
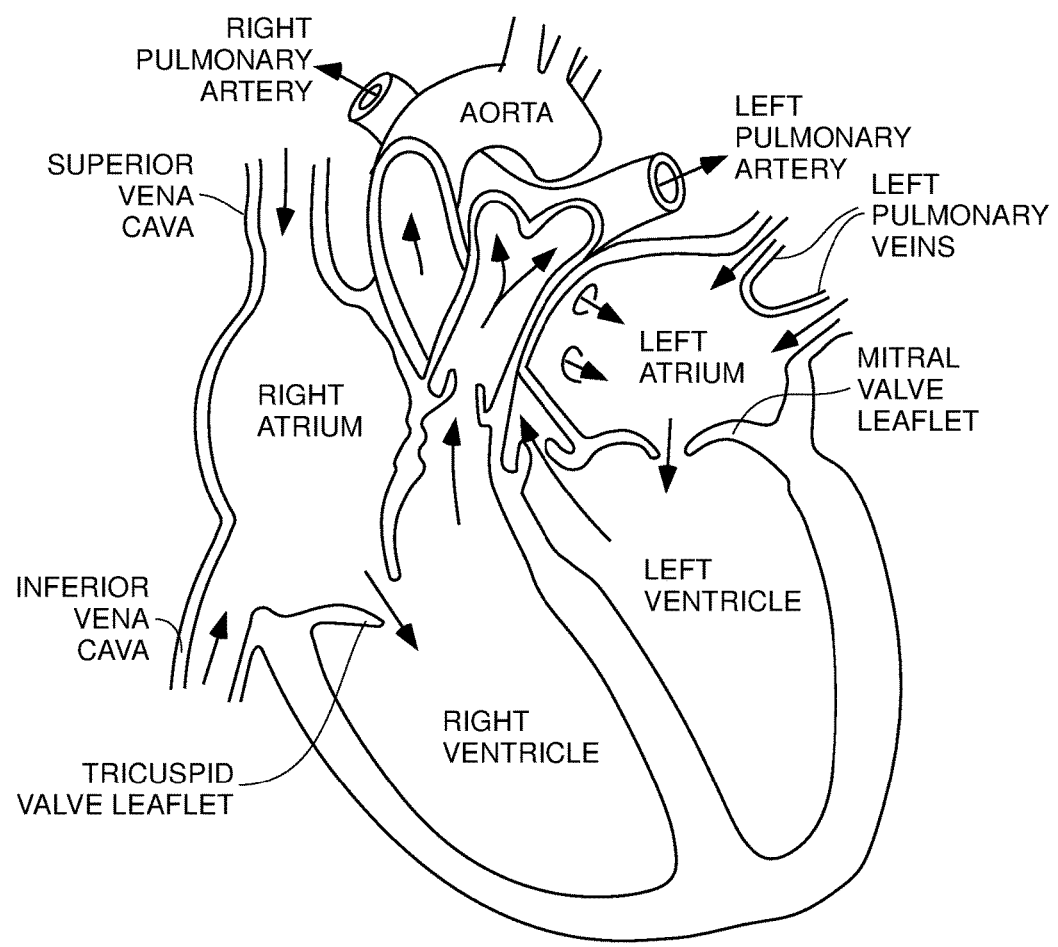
FIG. 1 illustrates certain features of the heart in cross-section.
Figure 2:
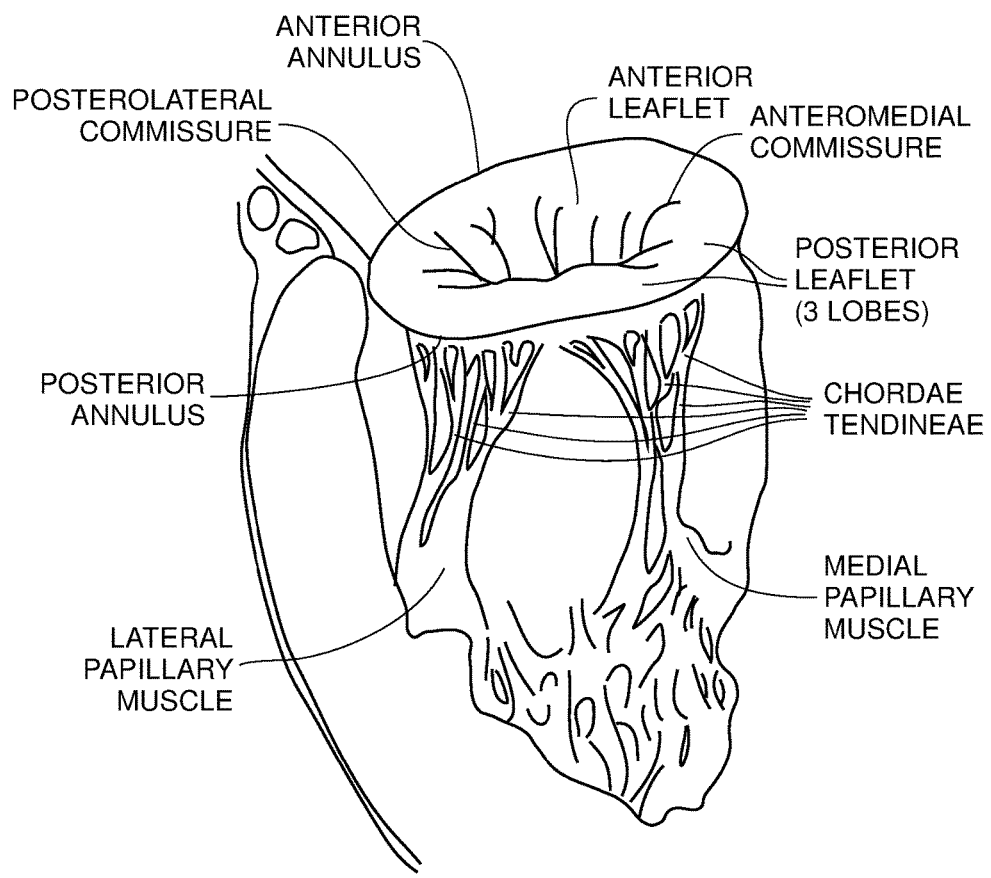
FIG. 2 illustrates a cross-sectional perspective view of the left side of the heart.
Figure 3:
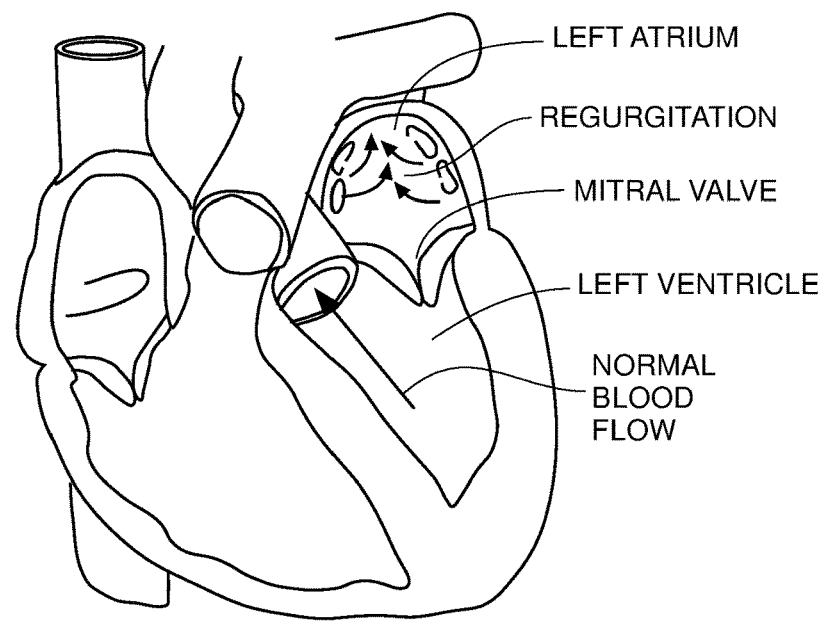
FIG. 3 illustrates a cross-sectional view of the heart showing retrograde blood flow resulting from mitral valve regurgitation compared with normal blood flow.
Figure 4:
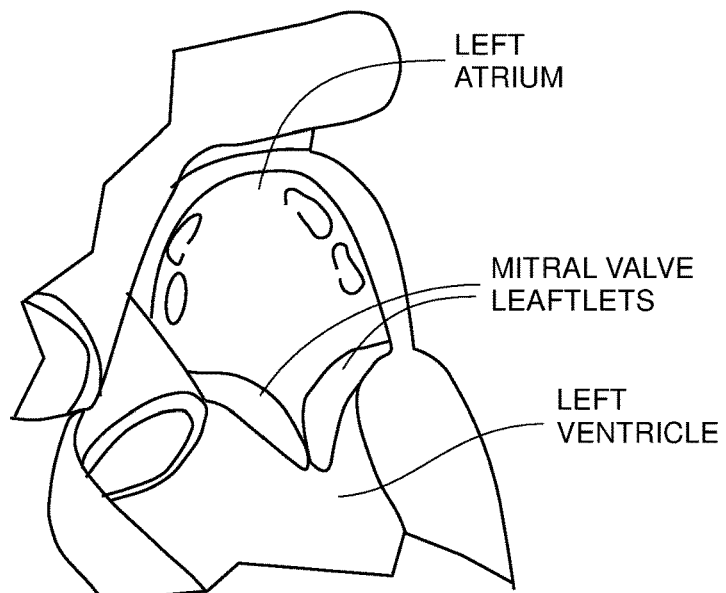
FIG. 4 illustrates a cross-sectional view of a portion of the heart showing prolapsing mitral valve leaflets and regurgitant blood flow.

Various embodiments of the present invention comprise a single-chamber anchoring solution that comprises (1) preservation of native valve functionality; (2) initial preservation of native valve functionality with subsequent full replacement of native valve functionality; (3) full replacement of native valve functionality; and (4) mitigation of the prolapsing distance of the dysfunctional leaflets by preventing the anterior excursion of the prolapsing leaflets above the upper annular surface and into the left atrial chamber in order to preserve native leaflet functionality for as long as possible.

As discussed, all known prosthetic heart valves are intended for full replacement of the native heart valve. Therefore, these replacement heart valves physically engage the inner annulus and/or valve leaflets, in many cases pinning the native leaflets against the walls of the inner annulus, thereby eliminating all remaining functionality of the native valve and making the patient completely reliant on the replacement valve. Generally speaking, when the native valve leaflets retain some functionality, preferred solutions are those that maintain and/or retain the native function of a heart valve, thus supplementation or augmentation of the native valve and its functionality is preferred rather than full replacement.

In certain cases, the native valve will have either lost virtually complete functionality before the interventional implantation procedure. In this case, the preferred solution provides a complete functionality replacement for the native valve.

In other cases, the native valve will retain some functionality following implantation of the prosthetic valve, but will continue to lose native functionality over time. Therefore, the preferred solution in these cases comprises delivery and implantation of a valve device that will function initially as a supplementary functional valve in order to preserve and retain native valve leaflet functionality as long as present, and over time progressively function as a replacement of the native function of a valve as is slowly loses native functionality. Thus, the preferred solution in these cases may initially preserve native valve functionality with only a low supplementing or augmenting support level required, while providing gradually increasing supplementing or augmenting support levels to accommodate an ever-increasing replacement demand as the native leaflet functionality slowly deteriorates. Ultimately, full replacement functionality may be provided by the preferred solution.

In this connection, it is a feature of various embodiments of the present invention to prevent the prolapsing valve leaflets from rising above the upper annular surface and into the left atrium to provide additional support for the native leaflet functionality and preservation of same for as long as possible.

Moreover, a single-chamber expanded and implanted device structure comprises certain embodiments as shown in the Figures. These embodiments of the expanded and implanted device structure may comprise, therefore, no structure that extends below a boundary, e.g., the annular plane as shown in the Figures and referred to in the art. Alternatively, no structure may extend below a defined boundary as discussed further, within the annular throat. Still more alternatively, certain embodiments may comprise no structure of the expanded and implanted device structure extending out of the heart chamber, e.g., the left atrium, into a blood vessel in fluid communication therewith, e.g., the pulmonary arteries as illustrated in the Figures.

Thus, in certain embodiments, the expanded and implanted structure in the left atrium may comprise no presence in, or engagement with, one or more of the patient's mitral valve comprising native leaflets, the left ventricle and a pulmonary artery.

Further, embodiments of the present invention may comprise a delivery of the collapsed prosthetic heart valve structure to the heart chamber, e.g., the left atrium, that comprises no presence in, or engagement with, one or more of the patient's mitral valve comprising native leaflets, the left ventricle, and a pulmonary artery.

The various embodiments of the present invention comprise preferred solutions for each of the above-described conditions.

Figure 5A:
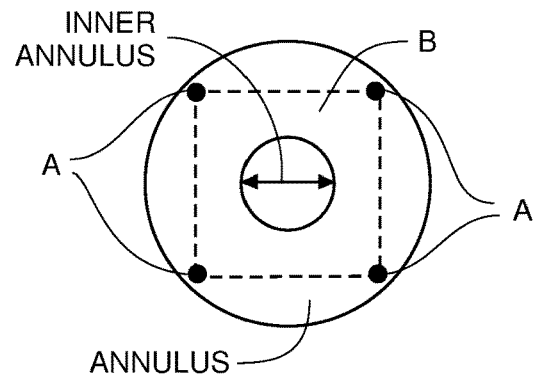
FIG. 5A illustrates a top view of the annulus and one embodiment of the present invention.
Figure 5B:
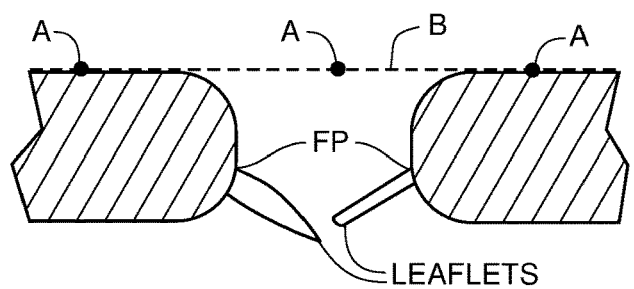
FIG. 5B illustrates a cross-sectional side view of the annulus and native leaflets and one embodiment of the present invention.
Figure 5C:
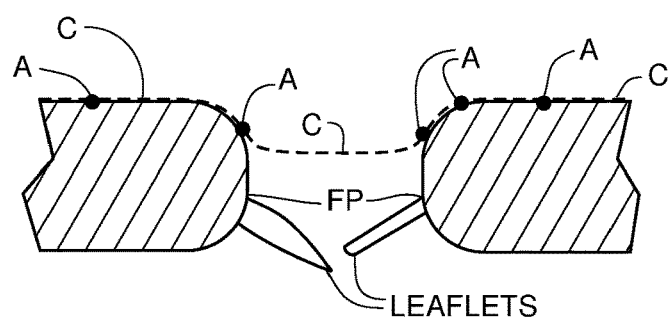
FIG. 5C illustrates a cross-sectional side view of the annulus and native leaflets and one embodiment of the present invention.

Referring now to FIGS. 5A-5E, a designated location or position of the upper surface of the annulus, or the upper annular surface, may be achieved by designating at least two points A, each of which must reside on the now-designated location of the upper annular surface. Plane B, best seen in FIGS. 5A and 5B, represents a plane that is generally flat and collinear with the at least two designated points A located on the designated upper surface of the annulus of the left atrium. A critical and required feature of the designated at least two points A requires they be located above the flexing point FP of the native valve leaflets. This arrangement, in turn, facilitates locating the lower-most portion of a structure extending across the annulus, or in some cases into the inner annulus. Therefore, a structure with a lower-most portion that is located on, or above, the designated at least two points will not adversely interfere with the remaining normal native valve functionality. The skilled artisan will recognize plane B as illustrated in FIG. 5B as residing generally on, or collinear with, what is commonly referred to as the annular plane, though as described below, other locations may be designated for the upper annular surface, each of which are within the scope of the present invention.

Further, the lowest point, or floor, of the left atrium and/or left atrial chamber relative to the annulus, including the inner annulus in certain embodiments, is defined herein as located by at least one line, either linear or curvilinear, connecting the designated at least two points A. Therefore, in the case of a curvilinear line or series of lines that may be curvilinear, the generally flat plane shown as plane B may form a curvilinear sheet C as shown in FIG. 5B and may comprise curvilinear variations across the sheet C.

A structure with a lower-most portion that is located at or above the defined and designated upper annular surface by the designated at least two points A, and the flat plane B or curvilinear sheet C connecting same, is defined herein as within the left atrium or left atrial chamber.

A structure located below the upper surface of the annulus as defined by the designated at least two points A and the plane B or curvilinear sheet C connecting same is defined herein as located outside of the left atrium or left atrial chamber.

The definition of the lower boundary of the left atrium relative to the annulus, and the corresponding definition of what is inside and what is outside the left atrium lower boundary has a single requirement beyond the designation of the at least two points and that is that the location of the designated at least two points A and the corresponding plane B or curvilinear sheet C cannot at any point adversely interfere with the functionality of the native valve leaflets. The remaining boundaries of the left atrium or left atrial chamber comprise the chamber walls and upper surface or roof as the skilled artisan will readily recognize. This definition of the boundaries of the left atrium or left atrial chamber now form the basis for locating and anchoring structures only within the left atrium or left atrial chamber, without any anchoring or other structure extending outside of the defined boundaries of the left atrium or left atrial chamber.

We note here that the lower-most portion of the various embodiments of the prosthetic heart valve device described herein may in some embodiments provide a barrier to the prolapsing mitral valve, thereby preventing prolapse to varying degrees depending on the depth within the inner annulus of the designated upper annular surface as described above. This is one of the inventive objectives of embodiments of the present invention. However, the lower-most structure of the various embodiments that may extend downwardly into the inner annulus must be located on or above the designed upper annular surface as defined herein.

It will be appreciated that, as shown in the Figures, the at least two designated points A, and the plane B or curvilinear sheet C connecting same are at all times located above the flexing point FP of the native leaflets. This is one of the features that allow, in some cases, prevention of prolapse of the native leaflets to varying degrees and at the same time enabling no adverse interference with the native leaflet functionality. Note in FIG. 5C that the portion of curvilinear sheet C extending across the annulus may curve or dip downward below what is commonly known as the annular plane so that the designated upper annular surface may include a downward extension or excursion into the inner annulus. This configuration is within the scope of the present invention so long as the curvilinear sheet C remains at all points in compliance with the requirements described above for the designated upper annular surface, e.g., located above the flexing point PF of the native leaflets so as to not hinder native functionality.

Alternatively, at least a portion of the lower surface 106 of base section 100 may also rest on a lower surface of the left atrium surrounding at least a portion of the annulus.

In a still more alternative set of embodiments, a portion of the designed upper annular surface may extend below the flexing point FP of the native leaflets while still preserving native functionality thereof, so long as at least partial coapting of the leaflets is enabled. Further, in the case where the native leaflet functionality is assessed to be very poor, the valve structure may extend downwardly through the inner annulus to effectively pin the native leaflets against the wall tissue. This will be a possible solution only in rare cases, but it is within the scope of the presently described invention. In this embodiment, the upper annular surface is also defined and designated at a location that is below the flexing point of the native leaflets.

Figure 5D:
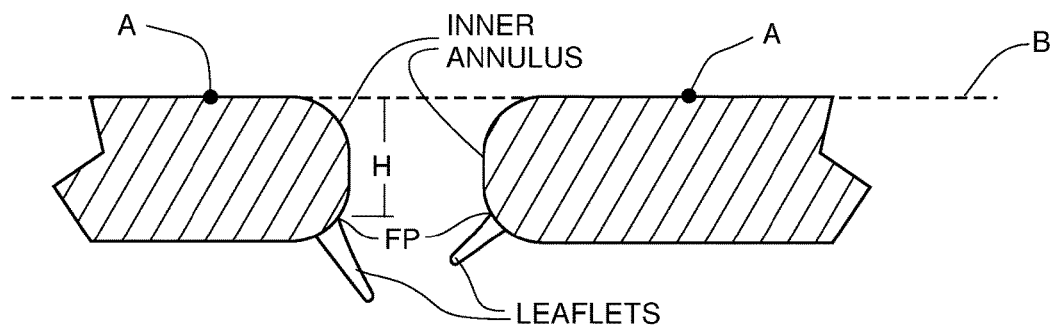
FIG. 5D illustrates a cross-sectional side view of the annulus and native leaflets and one embodiment of the present invention.
Figure 5E:
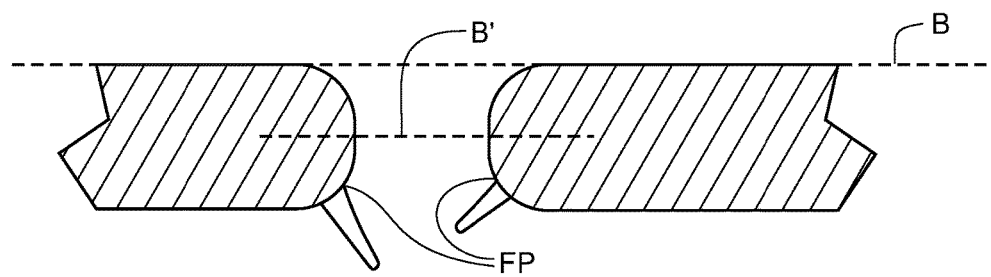
FIG. 5E illustrates a cross-sectional side view of the annulus and native leaflets and one embodiment of the present invention.

The relationship and definition of the upper surface of the annulus and the at least two designated points A and plane B is further illustrated in FIGS. 5D and 5E. There, the annulus is show in side cross-section with the inner annulus indicated as the interior channel of the annulus having a height H. FIG. 5D shows the upper surface of the annulus with corresponding plane B in a general alignment with the annular plane. FIG. 5E illustrates an alternative wherein the upper surface of the annulus is designated as slightly below the location in FIG. 5D and designated plane B'. However in each case, the upper surface of the annulus position and location designation as illustrated by plane B and/or curvilinear sheet C must be above the flexing point FP of the native leaflets so that the implanted lower surface 106 of the base section 100 which is to rest upon at least the upper surface of the annulus does not interfere with the native leaflet function. This alternative embodiment is to further illustrate that there is a plurality of points of designation A, with associated plane B or curvilinear sheet C, for positioning and locating the upper surface of the annulus and, therefore, for locating the lower surface 106 of the base section 100 upon implant.

Figure 6:
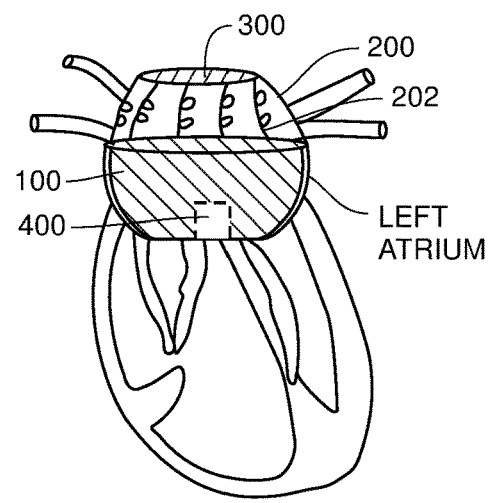
FIG. 6 illustrates a perspective view of one embodiment of the present invention.
Figure 7:
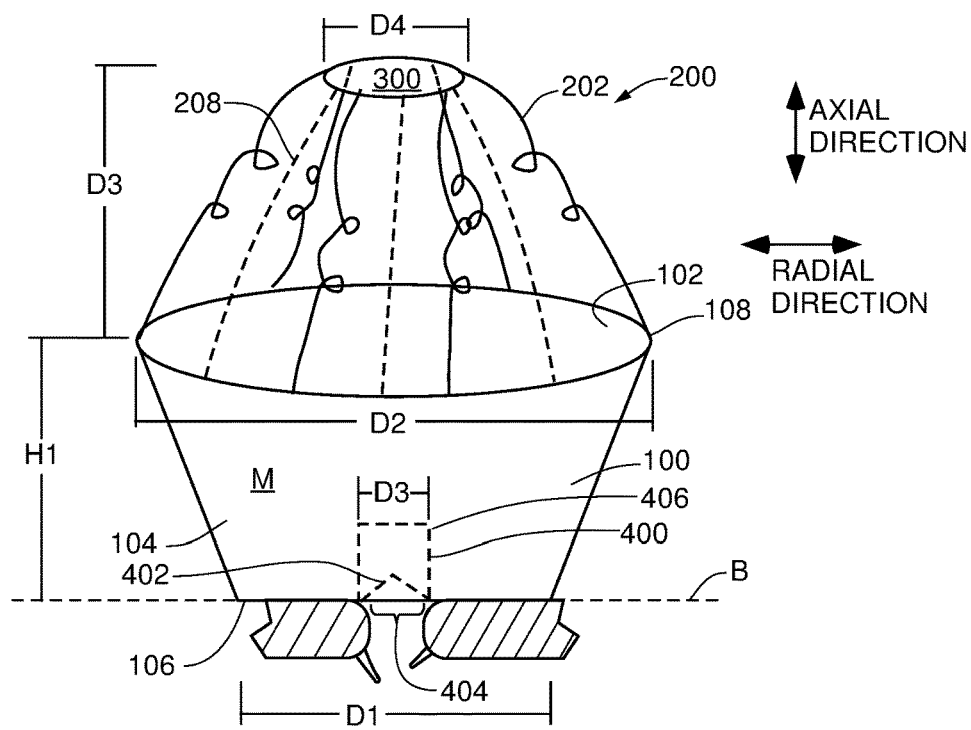
FIG. 7 illustrates a perspective view of one embodiment of the present invention.

Turning now to FIGS. 6 and 7, one embodiment of the present invention comprising a collapsible, and expandable, anchoring structure 10 comprising a base stent 100 with an expandable and collapsible web or cells as is known in the art, an intermediate spring-like section 200 and an atrial dome 300 is illustrated, wherein the intermediate spring-like section 200 is in operative connection with the base stent 100 and the atrial dome 300. FIG. 5 illustrates the anchoring structure 10 within the left atrium and without involvement, engagement or interference with structures outside the left atrium.

Base section 100 comprises an inner surface 102, an outer surface 104, a lower surface 106 having a diameter D1, an upper surface 108 having a diameter D2, and a height H1 defined generally as the vertical length between the lower and upper surfaces 106, 108. Base section 100 may comprise a stent, or other, construction that is capable of collapsing and expanding as is well known. Base section 100 preferably may be biased to expand to achieve the expanded state from a collapsed state, though other collapsed-to-expanded mechanisms may also be employed. Further, base section 100 may achieve a plurality of expanded states in order to expand and contract with the natural movements of the heart chamber walls and floor. Base section 100 may comprise a shape memory material, biased to achieve the expanded state(s) as in known in the art, e.g., nitinol or similar wire mesh construction or sliding element construction. Similarly, a shape memory polymer may be used for at least part of base section 100.

Preferably, when implanted in the left atrium, base section's outer surface 104, at least, is covered with a material M that conforms and seals with the atrial wall in at least the circumferential region of the wall that encompasses the left atrial appendage (LAA) within the left atrium in order to seal the LAA.

Figure 8:
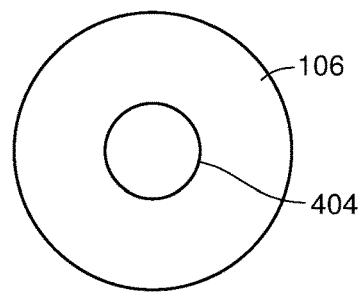
FIG. 8 illustrates a bottom view of one embodiment of the present invention.

FIGS. 6 and 7 illustrate the base section's lower surface 106 occupying the exemplary plane B discussed above as representing the designated upper annular surface, though other designations and locations are possible as also describe herein. The prosthetic one-way valve 400 is aligned generally with the annulus, to enable one-way fluid communication therethrough, and is located within the base section 100 and illustrated as residing generally on exemplary plane B representing the designated location of the upper surface of the annulus as discussed above. The prosthetic valve 400 comprises at least one leaflet, preferably two leaflets 402 and defines a one-way opening 404, as seen in FIG. 8, through the base stent lower surface 106 to facilitate fluid flow therethrough with subsequent flow into the annulus, while blocking reverse flow. Prosthetic one-way valve 400 may comprise a valve support device, e.g., a central cylinder 406 that is open to fluid flow and is in fluid communication with the atrial blood and the annulus when the one-way prosthetic valve is opened. Central cylinder 406 is configured to provide support and attachment for the valve leaflet(s) 402, the central cylinder 406 open to fluid flow received within the left atrium and, in some embodiments, configured to funnel or concentrate the received fluid flow toward the valve leaflet(s) 402.

Figure 9:
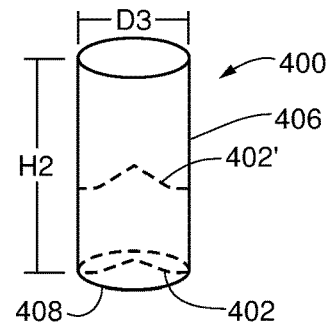
FIG. 9 illustrates a cutaway perspective view of one embodiment of the present invention.

As seen in FIG. 9, central cylinder 406 may comprise the valve leaflet(s) 402 arranged at or near the lower surface 408 of the central cylinder 406. Alternatively, the valve leaflet(s) 402 may be arranged and operationally connected at a point within the central cylinder 406 that is above the lower surface 408, with an exemplary embodiment illustrated by the dashed lines and 402'.

Alternatively, an aperture, e.g., the opening 404 of FIG. 8, may be substantially aligned with the annulus and arranged along the at least two designated points A, either within a plane B or along a curvilinear sheet C, and with prosthetic leaflets attached thereto may be provided to facilitate one-way valve functionality. Valve support device, e.g., the central cylinder 406, when present, comprises a height H2 that may be less than the height of base section 100, greater than height of base section 100 or equal to height of base section and a lower surface 408. Central cylinder 406 will also comprise a diameter D3 that is less than the diameters of both the lower and upper surfaces 106, 104 of base section 100.

Because the prosthetic one-way valve 400, specifically the lower surface 408 thereof, is not allowed to extend below the designated upper surface of the annulus as defined herein, the native valve functionality is preferably not eliminated or otherwise reduced except in rare cases described herein.

Figure 9A:
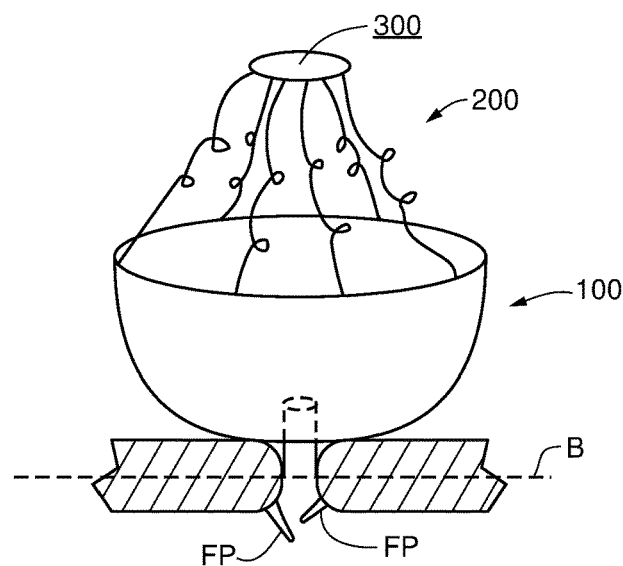
FIG. 9A illustrates a perspective view of one embodiment of the present invention.

It will be recognized that, in certain embodiments, the central cylinder 406 and valve leaflet(s) 402 supported therein, may be configured and positioned so that the lower surface 408 of the central cylinder 406 may extend below that of the lower surface 106 of the base section upon implantation. See FIG. 9A for an illustration of an exemplary embodiment. Again, with this arrangement, the valve leaflet(s) 402 may be located at any point along and within the central cylinder 406. However, in these embodiments, the central cylinder 406, including the lower surface thereon 408, is not positioned at a point that infringes, impinges or encroaches upon the native leaflet functionality in any way in order to meet one of the inventive objectives of preserving native leaflet functionality as long as possible. Stated differently, in this embodiment, the lower surface 408 of the central cylinder 406 may be located along the designated upper annular surface as defined by the at least two designated points and/or the corresponding plane B or curvilinear sheet C as defined herein, while the lower surface 106 of the base section 100 may be positioned at a point slightly above the designated upper annular surface, or the lower surface 106 of the base section 100 and the lower surface 408 of the central cylinder 406 may both be located on or above the designated upper annular surface.

Moreover, the central cylinder 406 may alternatively comprise a wide range of alternate leaf connecting structures and shapes besides a simple cylindrical profile, e.g., rectangle, oval, polygonal, cone profiles and others may be used while retaining the above-described functionality. Each of these alternatives are within the scope of the present invention.

Turning now to the intermediate spring-like section 200, the embodiments illustrated in FIGS. 6 and 7 comprise a plurality of spring elements 202, for example but certainly not limited to springs. The spring elements 202 as used within section 200 are defined herein as comprising any structure or device that may be non-elastically compressed and is used to store mechanical energy that results in a biasing force while the device is compressed. Thus, when the spring element 202 of the present embodiment is elastically compressed or stretched from its resting position, it exerts an opposing force that is roughly proportional to its change in length. Generally, the spring elements 202 of section 200 comprise a first end 204 and a second end 206, wherein the first end 204 of each spring element 200 is in operative connection with the base section 200 and the second end 204 of each spring element 202 is in operative connection with the atrial dome 300. When implanted, each of the spring elements 200 are preferably non-elastically compressed, as a result the spring elements 200 each exert forces tending to separate the atrial dome 300 from the base section 200, thereby seeking to increase the distance therebetween D3 to ultimately return the spring to its uncompressed and unstretched position of equilibrium. Thus, the distance D3 between the atrial dome 300 and the base section 200, when implanted, is less than the distance D3 between the atrial dome 300 and the base section 200 when not implanted and expanded and in certain embodiments when not implanted and collapsed. These forces are, in turn, transmitted between the atrial dome 300 and the atrial chamber's upper surface and the base section 200 and the upper surface of the annulus and/or the floor of the atrial chamber as well as, in certain embodiments, against the wall tissue of the atrial chamber.

Spring elements 202 are further preferably implanted in a compressive state that maintains some compression of the spring elements 202, so that the natural installation and expanded state within the atrial chamber comprises a biased generally upward and downward (axial) force set from the plurality of spring elements 200.

Spring elements 202 may be of an elastic or superelastic material such as shape memory, e.g., nitinol, polymer and the like. Alternatively, spring elements 202 may comprise a shock absorber construction, either mechanical or gas compression or any structure that allows non-elastic compression to store energy in order to provide a constant biasing force tending to separate the atrial dome 300 and the base section 200, and pressuring the atrial dome 300 and base section 200 into the tissue of the atrial chamber when implanted with the spring elements 202 in non-elastically compressed state.

The biasing forces produced by spring elements, in combination with a general complementary structural fitting between various aspects of the device 10, e.g., the base section's outer surface 104 and lower surface 106 and/or atrial dome 300, and the contours of the atrial chamber, e.g., the upper annular surface, the atrial chamber floor and/or the walls of the atrial chamber, allow the anchoring structure to remain in position within the left atrium without rotation or translation of at least the base section 100. In addition, in the various embodiments the spring elements 202, inter alia, may become at least partially endothelialized over time within the atrial wall tissue, providing additional anchoring support. This arrangement also allows flexional generally axial translation of the atrial dome 300 and base section 100 relative to each other and the spring elements 202 will allow some compliance flexing of the intermediate spring-like section 200 in a plurality of radial directions, thereby enabling the implanted prosthetic valve to move or comply with the natural movements of the heart.

Alternatively, as shown in FIG. 7, a plurality of spring elements 200 may be provided in combination, perhaps alternating, with rigid wires 208 having little or no expansion or contraction characteristics, may be provided between the base section 100 (in certain embodiments between the upper surface 108 of base section 100) and the outer surface 302, e.g., a wire boundary, of the atrial dome 300. This configuration may provide an upward expansion force bias to the structure while also tending to prevent substantial downward deflection or compression of the atrial dome 300 in relation to the base section 100. Alternatively, a plurality of only rigid wires 208 may be connected between the base section 100 (in certain embodiments between the upper surface 108 of base section 100) and an outer surface 302, e.g., a wire boundary, of the atrial dome 300. These rigid wires 208 may also endothelialize over time with the atrial chamber tissue providing additional anchoring support.

This arrangement may also allow firm anchoring within the left atrium while some enabling axial flexing of the atrial dome 300 relative to the base section 100 as well as flexing compliance of the intermediate spring-like section 200, though to a lesser extent, or a more controlled extent, than the spring member only embodiments.

Spring elements' second ends are operatively connected with an outer surface of a dome structure as shown. Dome, e.g., an atrial dome, may be formed from a wire boundary having a diameter and that is in connection with the second element of spring element and may comprise any closed geometric shape, e.g., circle, ellipse, triangle, polygon. Dome may comprise a diameter, or maximum distance, D4 across the dome structure that is preferably less than the diameter of the upper surface of the base.

One case may comprise the diameter, or maximum distance across the dome structure, being equal with the diameter of the central cylinder disposed within the base stent. In this case, a plurality of support wires or struts, either rigid or spring-like, or a combination thereof arranged in perhaps alternating fashion, may be operatively connected with the central cylinder and the wire boundary defining the dome structure in a substantially vertical alignment to provide further axial force and/or support, concentrating that axial expansion force in a relatively small area on the chamber roof surface, but wherein that force is not concentrated on a single point. Instead, the axial expansion force is distributed around the outer surface of the dome structure in the case of an open structure. Further, in some closed structure configurations, e.g., where the dome interior material is non-compliant or rigid as in a molded dome, the axial expansion force is also distributed throughout the interior material itself which is, in turn, pressing contact with the chamber roof. In the case where the dome is molded, a wire boundary may, or may not, be required. When not required, necessary connections are made directly with the molded material.

The atrial dome 300 may further comprise an open structure, i.e., with no interior material on the inside portion of the wire boundary or, as shown, may be closed, i.e., interior material covers the interior portion of the wire boundary, e.g., tissue, fabric and the like. Atrial dome 300 may comprise a flexible, compliant wire boundary, or may be rigid. Atrial dome 300 may further, in the case of a closed structure, comprise a flexible, compliant wire boundary in combination with a flexible interior material. Still more alternatively, dome may comprise, in a closed structure, a rigid compliant wire boundary in combination with a flexible interior material or a rigid interior material. Alternatively, closed structure embodiments of the dome may comprise a molded piece in a shape as illustrated or may comprise a circumferential lip surface extending downward from the dome's surface. The molded embodiment provides additional axial deflection/compression protection for the device.

Figure 10:
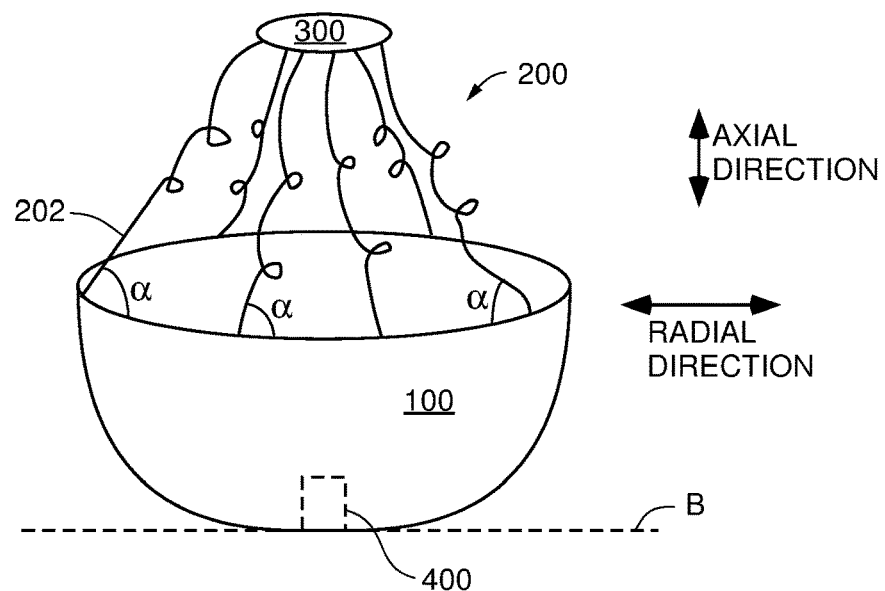
FIG. 10 illustrates a cutaway perspective view of one embodiment of the present invention.

Spring elements are illustrated in FIGS. 6 and 7 as generally conforming to the shape of the walls of the chamber, with a generally arching, concave profile with a slight inward angle α and with rigid wire members (when present) with slight inward angle α' that may be equal to, or may differ from, angle α. Alternatively, as in FIG. 10, the spring elements 202, and rigid wires when present, may be provided with a shorter length to achieve an inward angled orientation, of angle α, between the upper surface of base section 100 and outer surface, e.g., wire boundary, of atrial dome 300 in order to further maximize atrial force transmission from the biased spring elements 202 as well as pressure and friction fit of the device within the chamber. When rigid wires are present, they may also be angled with an angle α' that may be equal to, or that may differ from, angle α. Generally in the structure of FIG. 10, the angles α, α' will be more acute than the angles α, α' of the structure in FIGS. 6 and 7.

Moreover, base section 100 is in contact with, or may extend to, the upper annular surface and provides radial expansion force for achieving additional pressure and friction fit against the chamber surfaces.

Figure 11:
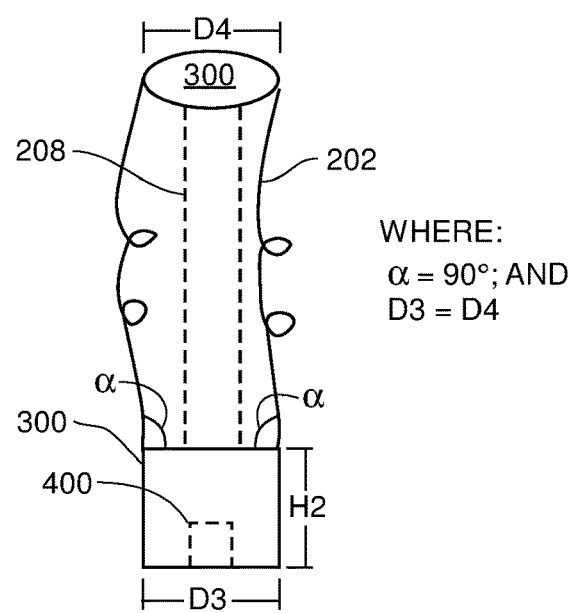
FIG. 11 illustrates a perspective view of one embodiment of the present invention.

FIG. 11 illustrates another alternate embodiment wherein the spring elements 202 and, when present the rigid wires, employ a concentration of axial forces in a relatively small area to maximize the pressure and friction fit achieved when expanded. Thus, the spring elements 202 and rigid wires, when present, are substantially at 90 degrees to the base section 100 which also contains the valve section 400 as in other embodiments. Thus, the axial force concentration is transmitted directly to the atrial dome 300, and distributed therearound when the dome 300 is an open construction and also through the atrial dome 300, when covered or laced with cross members such as struts and in particular when covering is a molded material. This axial force concentration is maximized when the support struts are angled with an essentially straight line connection from base stent to atrial dome circumference.

Figure 12:
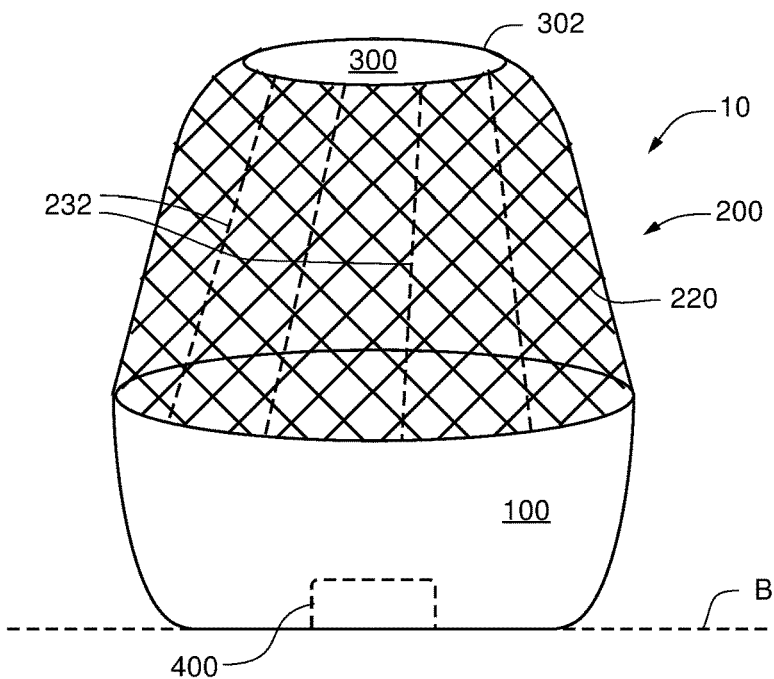
FIG. 12 illustrates a perspective view of one embodiment of the present invention.
Figure 13:
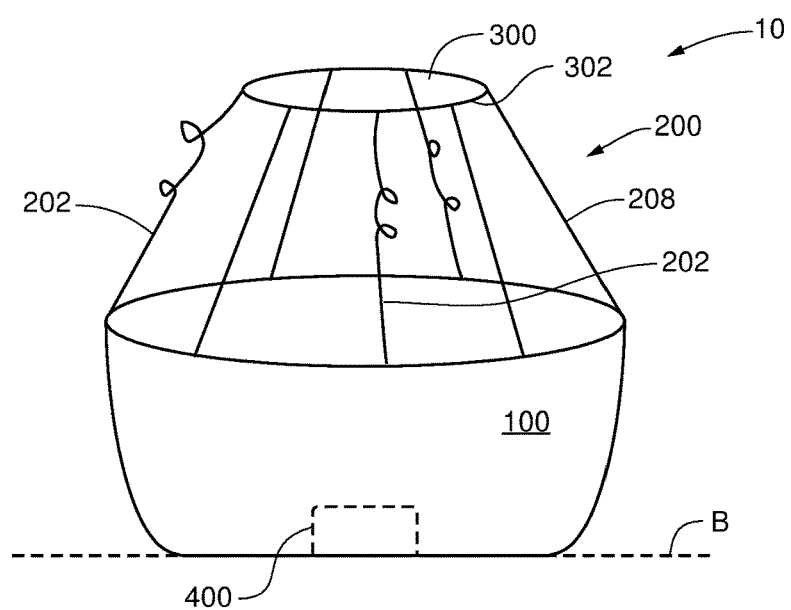
FIG. 13 illustrates a perspective view of one embodiment of the present invention.

FIGS. 12 and 13 illustrate an alternative anchoring structure 10 construction in that a flexible, and in some embodiments expandable mesh comprising the intermediate section 200, is shown connected with the upper surface of base section 100, rather than the spring element or spring element with rigid wires arrangements described above. The valve support 400, supporting in operative connection therein at least one prosthetic valve leaflet as discussed above, is shown as operatively connected within base section 100. The atrial dome structure 300 described above may be operatively connected with wire mesh and with the geometries and materials discussed with regard to the various embodiments herein. As described above, and as shown in FIG. 12, the atrial dome 300 may comprise a covered surface or as in FIG. 13, the atrial dome may comprise an open structure defined by an outer surface 302 or boundary, e.g., a wire boundary that will at least partially connect operatively with the heart chamber's upper surface or roof when the expandable structure is expanded and implanted. The boundary, e.g., wire boundary 302 may service as an attachment point for the flexible and expandable mesh material, particularly in the case of the open atrial dome embodiment. Alternatively, as described supra, the atrial dome 300 may comprise a covered region. Still more alternatively, the atrial dome 300 may comprise a separate structure attached to and lying on top of the wire mesh section, so that there is no opening or cutout in the top of the wire mesh section.

In addition, FIG. 13 illustrates the incorporation of the spring elements 202 and/or rigid wire elements 208 discussed above with the mesh of FIG. 12 (mesh not shown in FIG. 13). In this connection the spring elements 202 and/or rigid wire elements 208 may be disposed on the interior surface of the mesh and/or on the exterior surface of the mesh. Alternatively, spring elements and/or rigid wires may be integrated into, or woven through, the mesh structure and, as described above, be connected between the base section and the atrial dome.

FIG. 12 also illustrates an alternate structure that assists in transmission of axial force to the atrial dome 300, and distributed therearound when the dome 300 is an open construction and also through the atrial dome 300, when covered and in particular when covering is a molded material. Thus, in this alternate embodiment, struts 222 are shown in dashed lines to provide direct transmission of axial forces between the base section 100 and the atrial dome 300 to assist in anchoring. Struts 222 may be rigid or may comprise some axial compliance and/or radial flexibility.

Further, the rigid and/or spring-like support elements discussed above that, when present, may operatively connect between the central cylinder and dome may be included with the wire mesh construction of FIG. 12. Still more alternatively, the rigid and/or spring-like support elements, if present, may connect the central cylinder directly with the wire mesh, in a substantially vertical orientation as viewed from a front or side view as discussed above, in embodiments where the dome structure is not included.

Each of the embodiments discussed and illustrated herein may further comprise an expanded and implanted structure that does not extend into a lumen of, or otherwise engage, the pulmonary artery(ies).

Therefore, generally the devices described herein will re-establish substantially complete valve functionality, while preserving the remaining native valve functionality, by preventing the regurgitant flow from reaching the exemplary left atrium and gradually increasing the augmentation or supplementation of the slowly deteriorating native valve and/or leaflets until substantially total replacement function is achieved.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A prosthetic heart valve device for expanded implantation within a heart chamber having a chamber roof, the heart chamber in fluid communication with an annulus comprising an annular plane and with a native valve having leaflets, the device comprising:
   a base section comprising a lower surface that is at least partially disposed on the annular plane;
   an atrial dome section configured to be in pressured and frictional engagement with the chamber roof when the device is expanded and implanted;
   an intermediate section comprising a flexible and expandable mesh and operatively attached to the base section and the atrial dome section in operable connection with the base frame and top section; and
   a central cylinder valve support comprising a lower surface, the central cylinder valve support operatively attached to the base section and comprising at least one prosthetic valve leaflet operatively attached therein, wherein the lower surface is located on or above the annular plane.

2. The device of claim 1, further comprising the at least one prosthetic valve leaflet attached within the central cylinder valve support at the lower surface of the central cylinder valve support.

3. The device of claim 1, further comprising the at least one prosthetic valve leaflet attached within the central cylinder valve support at a point that is located above the lower surface of the central cylinder valve support.

4. The device of claim 1, wherein the heart chamber comprises the left atrium and the native valve comprises the mitral valve comprising native leaflets.

5. The device of claim 4, further comprising the expanded and implanted device comprising no structural presence in, or engagement with, one or more of the group consisting of: the native mitral valve comprising native leaflets, the left ventricle, and a pulmonary artery.

6. The device of claim 1, further comprising the expanded and implanted device comprising no structural engagement presence in, or engagement with, with the native valve leaflets.

7. The device of claim 1, wherein the atrial dome section comprises a wire boundary.

8. The device of claim 1, wherein the atrial dome section comprises an open structure defined by the wire boundary.

9. The device of claim 1, wherein the atrial dome section comprises a covered structure defined by a wire boundary.

10. The device of claim 1, the intermediate section comprising one or more struts operationally connected between the base section and the atrial dome.

11. The device of claim 1, the intermediate section further comprising a plurality of spring elements comprising springs or shock absorbers operationally connected between the base section and the atrial dome.

12. A method for preserving the functionality of a patient's at least partially malfunctioning native heart valve with an implanted prosthetic heart valve device within a heart chamber comprising an annulus defining an annular plane, comprising:
   providing the prosthetic heart valve device of claim 1;
   expanding and implanting the prosthetic heart valve device within a single heart chamber wherein the heart chamber is at least partially protected from retrograde flow by the at least partially malfunctioning native valve; and preserving the remaining normal native functionality of the at least partially malfunctioning native valve with the expended and implanted prosthetic heart valve device.

13. The method of claim 12, wherein the single chamber of the heart comprises the left atrium and the native valve is the mitral valve comprising native leaflets.

14. The method of claim 13, comprising ensuring the expanded and implanted prosthetic heart valve device has no structural presence in, or engagement with, at least one of the group consisting of: the mitral valve comprising native leaflets, the patient's left ventricle, and a pulmonary artery.

15. A method for preserving and supplementing the functionality of a patient's at least partially malfunctioning native heart valve with an implanted prosthetic heart valve device within a heart chamber comprising an annulus defining an annular plane, comprising:

providing the prosthetic heart valve device of claim 1;

expanding and implanting the prosthetic heart valve device within a single heart chamber wherein the heart chamber is at least partially protected from retrograde flow by the at least partially malfunctioning native valve; and preserving and supplementing the remaining normal native functionality of the at least partially malfunctioning native valve with the implanted prosthetic heart valve device.

16. The method of claim 15, wherein the single chamber of the heart comprises the left atrium and the native valve is the mitral valve.

17. The method of claim 16, further comprising ensuring the expanded and implanted prosthetic heart valve device has no structural presence in, or engagement with, at least one of the group consisting of: the mitral valve comprising native leaflets, the patient's left ventricle, and a pulmonary artery.

18. A method for preserving and supplementing any remaining native functionality of a patient's at least partially malfunctioning native heart valve and replacing the heart valve functionality with an implanted prosthetic heart valve device with an implanted prosthetic heart valve device within a heart chamber comprising an annulus defining an annular plane, comprising:

providing the prosthetic heart device of claim 1;

expanding and implanting the prosthetic heart valve device within a single heart chamber wherein the heart chamber is at least partially protected from retrograde flow by the at least partially malfunctioning native valve;

preserving and supplementing the remaining normal native functionality of the malfunctioning native valve with the implanted prosthetic heart valve device; and completely replacing the native valve functionality when the native valve ceases to provide any normal native functionality.

19. The method of claim 18, wherein the single chamber of the heart is the left atrium and the native valve is the mitral valve comprising native leaflets.

20. The method of claim 19, further comprising ensuring the expanded and implanted prosthetic heart valve device has no structural engagement with at least one of the group consisting of: the native mitral valve comprising leaflets, the patient's left ventricle, and a pulmonary artery.

* * * * *